United States Patent [19]

Dubbeldam

[11] Patent Number: 4,908,508

[45] Date of Patent: Mar. 13, 1990

[54] PROCESS AND APPARATUS FOR DETERMINING THICKNESSES OF LAYERS

[75] Inventor: Gerrit C. Dubbeldam, Zevenaar, Netherlands

[73] Assignee: Akzo N.V., Arnhem, Netherlands

[21] Appl. No.: 137,346

[22] Filed: Dec. 23, 1987

[30] Foreign Application Priority Data

Feb. 12, 1987 [NL] Netherlands .................. 8700337

[51] Int. Cl.$^4$ ............................................. G01B 11/06
[52] U.S. Cl. ................................... 250/225; 250/560; 356/369; 356/381
[58] Field of Search ............... 356/369, 364, 381, 382; 250/225, 560; 364/563

[56] References Cited

U.S. PATENT DOCUMENTS

| | | | |
|---|---|---|---|
| 2,556,344 | 6/1951 | Silge | 356/135 |
| 2,666,355 | 1/1954 | Trurnit | |
| 3,017,512 | 1/1962 | Wolbert | 356/382 |
| 4,585,348 | 4/1986 | Chastang et al. | 356/369 |
| 4,672,196 | 6/1987 | Canino | 250/225 |
| 4,725,145 | 2/1988 | Azzam | 356/369 |

FOREIGN PATENT DOCUMENTS

| | | |
|---|---|---|
| 0067921 | 12/1982 | European Pat. Off. |
| 0073980 | 3/1983 | European Pat. Off. |
| 2153071 | 8/1985 | United Kingdom |

OTHER PUBLICATIONS

Kinetics of Protein Adsorption and Immunological Reactions at a Liquid/Solid Interface by Ellipsometry; Azzam, Rigby and Krueger; Phys. Med. Biol. 1977, vol. 22, No. 3, 422-430.
Smith et al, "Determination of the Thickness and Refractive Index of Films on Silicon Using Split-Beam Ellipsometry", Solid State Electronics, vol. 12, (1969), pp. 765–774.
Arwin et al, "A Reflectance Method for Quantification of Immunological Reactions on Surfaces", Analytical Biochemistry, 145, (1985), pp. 106–112.
Hauge et al, "Design and Operation of ETA, an Automated Ellipsometer", IBM J. Res. Develop., Nov. 1973, pp. 472–489.
Arwin and Lundstrom, *Analytical Biochemistry*, 145 (1985), pp. 106–112.

*Primary Examiner*—Edward P. Westin
*Attorney, Agent, or Firm*—Oliff & Berridge

[57] ABSTRACT

A process for determining the thickness and/or change in thickness of a thin layer applied to a carrier, the process comprising radiating the carrier coated with the thin layer with a plane polarized light beam at a single incident angle and detecting the reflectance on the carrier and layer. The light reflected by the carrier and the thin layer is split into a p-polarized part and an s-polarized part, after which the respective intensities $(I_s)_r$ and $(I_p)_r$ of the reflected s-polarized light and p-polarized light are measured simultaneously for the two parts, and calculating a quantity M according to the equation:

$$M = \frac{(I_s)_r - (I_p)_r}{(I_s)_r + (I_p)_r} = \frac{R_s - mR_p}{R_s + mR_p}$$

in which formula
$R_s$ is the ratio of the intensities $(I_s)_r$ and $(I_s)_i$ of the reflected and incident s-polarized light, respectively;
$R_p$ is the ratio of the intensities $(I_p)_r$ and $(I_p)_i$ of the reflected and incident p-polarized light, respectively;
m is the ratio of the intensities $(I_p)_i$ and $(I_s)_i$ of the incident p- and s-polarized light, respectively; and the quantity
M is a function of the thickness of the thin layer.

20 Claims, 2 Drawing Sheets

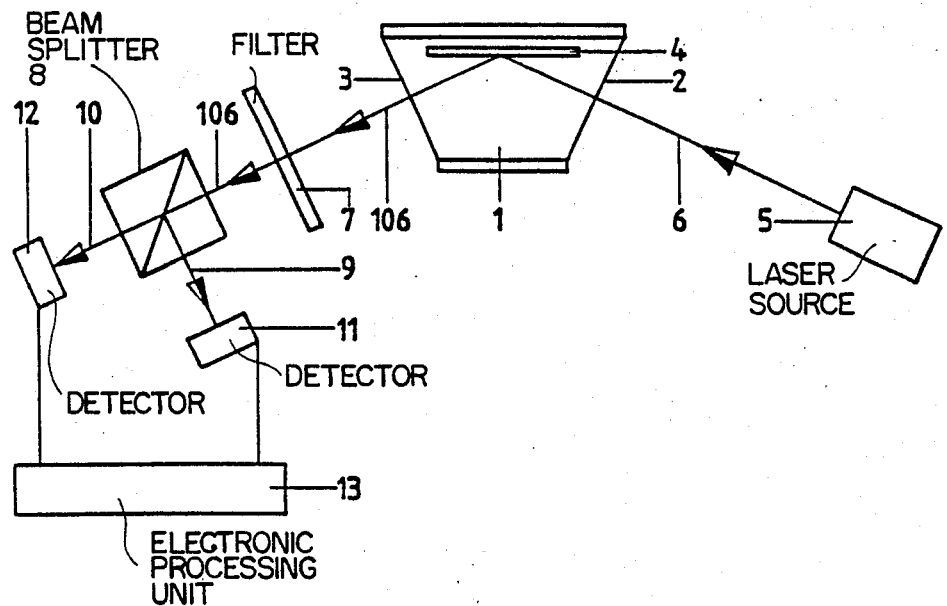
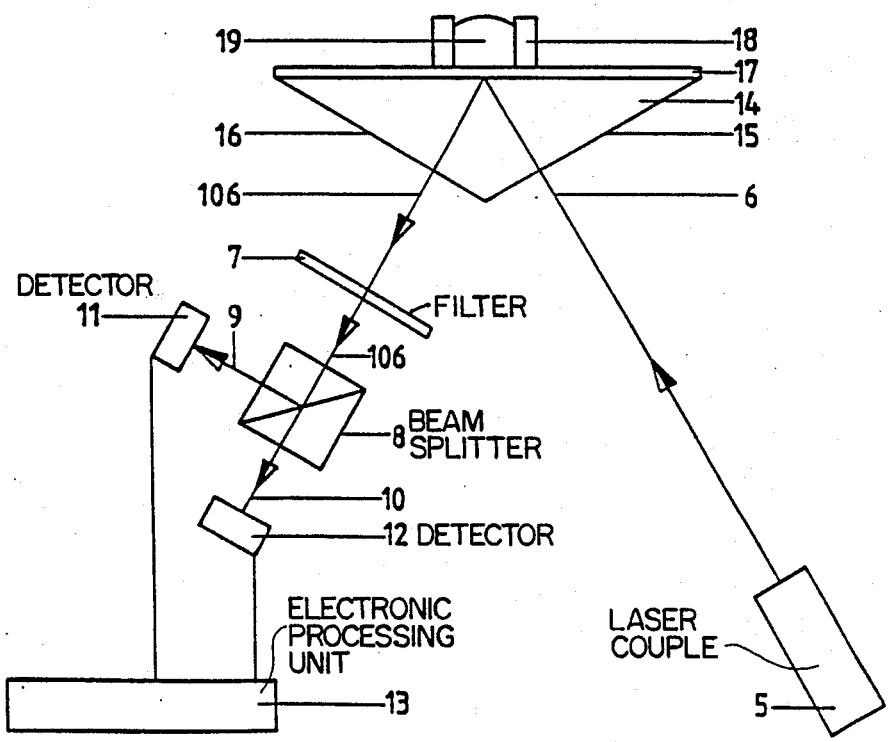

PROCESS AND APPARATUS FOR DETERMINING THICKNESSES OF LAYERS

BACKGROUND OF THE INVENTION

1. Field of the Invention:

The invention relates to a process for determining the thickness and/or change in thickness of a thin layer applied to a carrier, in which the carrier coated with the thin layer is radiated with a plane polarized light beam and the reflectance on the carrier and layer is detected, after which the measured amount of detected light is converted into a layer thickness and/or change in layer thickness. The invention also relates to the use of this process for determining protein/carrier and protein/protein interactions, as well as to a means for carrying out such a process.

2. Description of the Related Art:

A process as described above and application thereof for quantification of immunological reactions on surfaces is known from an article in Analytical Biochemistry 145 (1985), pp. 106–112. In this well-known method, light polarized in the plane of incidence at an angle virtually equal to the (pseudo) Brewster angle, is directed to the carrier. The intensity of the reflected light is measured. With the build-up of a thin layer on the carrier, the reflection value of the reflectance will change, and hence so will the intensity. Thus, the change in intensity forms a measure of the thickness of the thin layer.

To the known process there is the problem of its being susceptible to fluctuations in intensity of the light source used, because a change in intensity is used as a direct measure of (a change in) thickness. Although this source of error may be eliminated to a considerable extent by e.g. the use of reliable laser light sources such as a helium-neon laser, which provides a high intensity at a stable wave length, the intensity dependence of the process does lead to restrictions in this way, considering that a helium-neon laser is not necessarily universally applicable. Also, in the well-known method of calculating the measuring sensitivity, both the intensity of the light beam and the reflection and transmission properties of all optical components in the optical path will have to be known.

Processes for determining layer thicknesses in which the measuring results do not directly vary with the intensity of the light reflected by the substrate are known in themselves from a great many publications. Those processes, however, are always particular embodiments of ellipsometry determinations. The drawback to such processes is that for the determination of every layer thickness two measurements are required which are carried out at separate moments at different settings of the analyzer. In IBM J. Res. Develop. of November 1973, pp. 472–489 it has been suggested that the analyzer be rotated, so that the time interval between the two measurements can be considerably reduced. But there still remains the drawback of requiring a computer program for the determination of the layer thickness.

U.S. patent specification No. 2,666,355 describes a continuous determination of the layer thickness using a conventional ellipsometer. Although in the determination by it of the growth of a protein layer, different measuring settings are not required for each determination and the intensity of the reflected light appears to be a measure of the thickness of the thin layer, such a method offers hardly any advantages, if at all, over the aforementioned method discussed in Analytical Biochemistry.

Finally, mention is made of an article by Smith et al. in Solid State Electronics. Vol. 12, No. 10, October 1967, Pergamon Press, pp. 765–774. The article mentions a polarizing beam splitter for the separation of p- and s-polarized beam which is totally different from that envisaged by the process of the present invention. For, the known process has for its object to readily obtain two light beams of equal intensity merely by setting the analyzer. By applying the same procedure to incident light and rotating the detector assembler through 45°, the ellipticity parameters $\Delta$ and $\Psi$ can be determined from the different angular position of the analyzer. So it is not possible for this process to be used for continuous determination of the layer thickness.

SUMMARY OF THE INVENTION

The present invention is directed to a process and apparatus for determining the thickness and/or change in thickness of a thin layer applied to a carrier, the process comprising radiating the carrier coated with the thin layer with a plane polarized light beam at a single incident angle, detecting the reflectance on the carrier and layer, splitting the light reflected by the carrier and the thin layer into a p-polarized part and an s-polarized part, after which the respective intensities $(I_s)r$ and $(I_p)r$ of the reflected s-polarized and p-polarized light are measured simultaneously for the two parts, and calculating a quantity M according to the equation:

$$M = \frac{(I_s)_r - (I_p)_r}{(I_s)_r + (I_p)_r} = \frac{R_s - mR_p}{R_s + mR_p},$$

in which
$R_s$ is the ratio of the intensities $(I_s)_r$ and $(I_s)_i$ of the reflected and incident s-polarized light, respectively;
$R_p$ is the ratio of the intensities $(I_p)_r$ and $(I_p)_i$ of the reflected and incident p-polarized light, respectively;
m is the ratio of the intensities $(I_p)_i$ and $(I_s)_i$ of the incident p- and s-polarized light, respectively; and the quantity
M is a function of the thickness of the thin layer.

The apparatus according to the present invention comprises a cell for containing liquid, a substrate provided in the liquid for carrying the layer, a beam splitter, a laser source for directing a plane polarized beam toward the substrate, the plane polarized beam being reflected by the substrate and the layer toward the beam splitter, the beam splitter splitting the reflected polarized beam into a p-polarized beam and an s-polarized beam, a first detector for detecting an intensity of the p-polarized beam and a second detector for detecting an intensity of the s-polarized beam.

By measuring according to the invention both the reflection of p-polarized radiation and that of s-polarized radiation, and by adroitly combining the measuring data obtained, the resulting signal will be insensitive to the intensity of the radiation source. An additional advantage is that the process according to the invention has a greater sensitivity to variations in layer thickness, and that it is possible for the process to be carried out within a wide linear measuring range. In determining the growth of a protein layer, the measuring result is independent—within wide limits—of the thickness and the index of refraction of a layer previously applied to the carrier.

In the formula for the quantity M, which is a function of the thickness of the thin layer, the variable parameter m constitutes the ratio of the intensity of the incident p-polarized light to the intensity of the incident s-polarized light. This ratio may be changed by varying the angle of the polarization direction of the plane polarized light with the plane of incidence. If the source of light is a laser, this may easily be achieved by rotating the laser about its axis.

The process according to the invention may be used e.g. by directing a plane polarized laser beam to a substrate at the Brewster angle and passing the reflected beam through a polarizing beam splitter in the reflected beam, which separates the p-polarization and the s-polarization. Thus, the p-reflection and the s-reflection may be measured simultaneously using two separate photo detectors. The difference between the two reflections is divided electronically by their sum. The final signal is a measure of the thickness of a layer on the substrate.

The process according to the invention is particularly suited to measuring layer thicknesses or to establishing changes in the thickness of layers of organic material. In a preferred embodiment of the process according to the invention use is made, for determining the degree of growth of organic layers on a carrier, of a carrier previously coated with a thin layer of a transparent inorganic material or of an organic polymer of such a thickness that there is an almost linear relation between the quantity M and the thickness of the organic layer built up on the previously applied thin layer. Use is made here, in a suitable manner, of a carrier which is coated with a thin layer of an organic polymer of a thickness of about 0.15 $\lambda/n$, with $\lambda$ being the wavelength of the light and n being the index of refraction of the polymer.

It has been found that above a certain thickness value, the relationship between the quantity M measured according to the invention and the thickness of a layer present on a substrate is virtually linear over a fairly wide range. If the process is used to determine whether or not organic layers, e.g. protein layers from a protein solution, have formed, it is preferred for accuracy that the measurement be carried out in said linear area. This can be done by first applying to the substrate, which may be a silicon or glass slide, a thin layer of an inorganic material such as quartz or a thin layer of an organic polymer such as polystyrene or nylon. Using polystyrene with a thickness of the polystyrene layer of over 40 nm, e.g. about 50 nm, and using a He-Ne laser (wavelength 632.8 nm) as a light source, will result in the preferred linear relation between the quantity M and the thickness of a layer formed on the polystyrene.

For carrying out the process according to the invention, several variants may be used. In a first variant a substrate is placed in a cell containing the solution which is to be examined, and through the wall of the cell a laser beam is directed to the substrate at the desired angle. The reflected beam is received outside the cell and processed in the aforementioned way. This first variant does not give quite satisfactory results for direct measurements in cloudy liquids. In such cases it is preferred that use be made of a second variant of the process according to the invention, in which a prism is used as the carrier or substrate, and in which the light, e.g. a laser beam, is directed to the prism in such a way that it will enter and leave through the respective lateral faces and be reflected on the base face on which the thin layer is present.

In the first variant, in which a substrate is placed in a cell, use may be made in a suitable way of a helium neon laser as the light source and a silicon slide as the substrate. As silicon is impervious to the radiation of a helium neon laser, the second variant cannot be carried out with such a laser and a silicon prism. Instead, another laser, e.g. a semiconductor laser emitting radiation at 1.53 $\mu$m, may be used. Alternatively, use may be made of a glass prism, preferably of the highest possible index of refraction.

The process according to the invention may find very suitable application for determining certain interactions, such as protein/carrier and protein/protein interactions. Then the process according to the invention is applied a number of times using, in succession, different protein solutions. In experiments in which the process according to the invention was applied, a substrate, which had been coated with a thin layer of polystyrene of about 50 nm, was successively brought into contact with three protein solutions, viz. anti-HCG, BSA and HCG. On the thin layer of polystyrene there was found to occur a growth of anti-HCG. In the solution with BSA, no change in thickness was found to occur and in the solution with HCG an increase in layer thickness took place. Thus, the presence of HCG could be demonstrated, provided that use is not made of a known HCG solution but of a solution which is suspected to contain HCG. A suitable means for use in said application of the process according to the invention is a plate-shaped or prism-shaped carrier, one surface of which is coated with a thin layer of an organic polymer material, e.g. polystyrene, of a thickness of at least 40 nm. With such carriers, said process may be carried out in the linear measuring range.

BRIEF DESCRIPTION OF THE DRAWINGS

The invention will be further described with reference to the accompanying drawings in which:

FIG. 1 is a schematic representation of a measuring arrangement for carrying out a first variant of the process according to the invention, FIG. 2 is a similar representation of a second variant.

DESCRIPTION OF THE PREFERRED EMBODIMENTS

Figure 3:
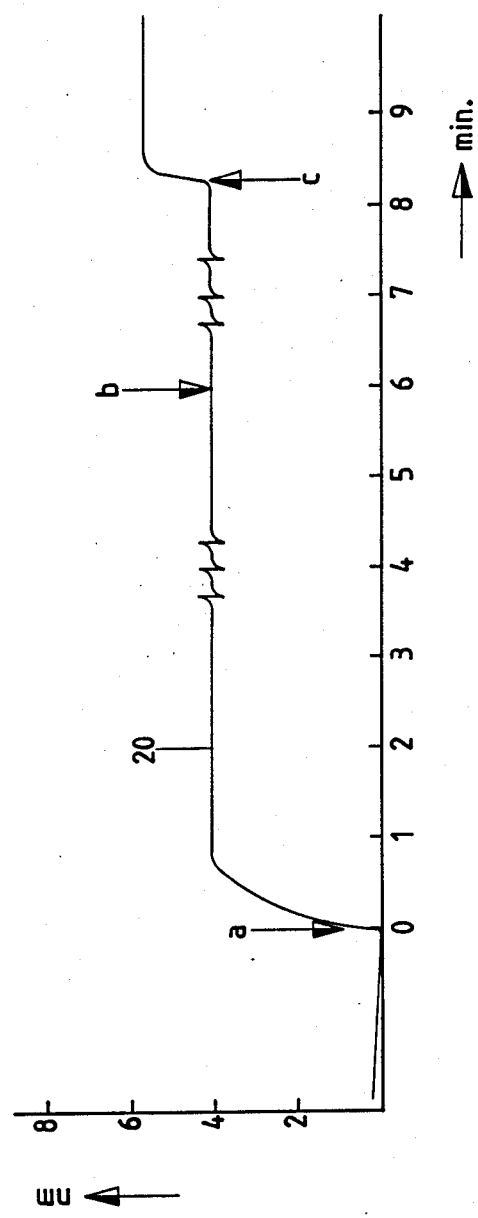
FIG. 3 is a graph in which the increase in layer thickness is plotted against time for the use of the second variant of the process according to the invention.

FIG. 1 is a plan view of a schematically represented measuring arrangement comprising a cell 1 equipped with windows 2 and 3, which constitute the side walls of the cell 1. In the cell 1 is contained a liquid, e.g. a protein solution, and in the cell and the liquid is placed a substrate 4. The substrate 4 may be e.g. a silicon slide coated with a layer of polystyrene of about 60 nm. By a laser source 5, e.g. a helium neon laser, a polarized beam 6 is directed through the window 2 to the substrate 4. The set-up is such that the beam 6 hits the substrate 4 virtually at the Brewster angle. The beam 6 is reflected on the substrate 4 and a thin layer which may be present on it, and leaves the cell 1 by the window 3. Via a suitable filter 7 the reflected beam 106 hits the polarizing beam splitter 8, by which the beam is split into a p-polarized beam 9 and an s-polarized beam 10. These beams 9 and 10, respectively, are subsequently received by the detectors 11 and 12, respectively. The detectors are connected to a schematically indicated electronic processing unit 13, which derives from the detector signals a quantity $M=(R_s-mR_p)/(R_s+mR_p)$. For the ratio between the reflected p-polarized and s-polarized light to be in equilibrium, the polarization direction of the plane polarized laser beam 6 is chosen in such a way that the ratio of the intensities of the p-polarized beam 9 and the s-polarized beam 10 is 3:1. In that case the measuring value M determined by the electronic unit 13 corresponds to: $M=(R_s-3R_p)/(R_s+3R_p)$. This situation is obtained if the polarization direction of the laser beam 6 is at an angle of 30° to the plane of incidence. This quantity M is intensity-independent and is a function of the thickness of a layer present on the substrate 4. In the absence of a layer on the substrate 4, $R_p=0$ and $M=1$, since the beam 6 hits the substrate at the Brewster angle. The relation between the layer thickness and M appears to be virtually linear at a layer thickness of from about 40 nm. For investigation into the growth of relatively thin protein layers, it is therefore recommended that the substrate 4 be coated with a layer of polystyrene of about 50 nm. This may be done for instance by spincoating.

Although satisfactory results may be achieved using the measuring arrangement according to FIG. 1, measurement with it in cloudy or absorbing liquids is hardly possible if at all. Moreover, this method requires a relatively large amount of solution. These disadvantages may be avoided by measuring the reflection via the substrate, so that the light no longer passes through the solution. A suitable measuring set up for this is depicted schematically in FIG. 2. In this figure and in FIG. 1 like parts are referred to by like numerals.

In FIG. 2 the substrate 14 is an equilateral prism, which may be made of e.g. heavy flint glass ($n_D=1.784$). The equal planes 15 and 16 of the prism 14 are provided with an anti-reflection coating. The base face is coated with a thin layer 17 of polystyrene (thickness about 50 nm). Such a layer may be obtained by spin-coating.

The prism 14 is cut in such a way that at right angles of incidence to the lateral faces, the light will hit the base face at the Brewster angle for the interface of glass-water (37°). For the ratio between the reflected p-polarized light and the s-polarized light to be in equilibrium, such a polarization direction is arranged of the plane polarized beam 6 of the helium neon laser 5 as will result in a ratio of the intensities of the p-polarized beam 9 and the s-polarized beam 10 of 50:1. In that case the value M measured by the electronic unit 13 is $M=(R_s-50R_p)/(R_s+50R_p)$, provided that the polarization direction of the laser beam 6 is at an angle of 8.05° to the plane of incidence.

On the base face of the prism 14 is placed a ring 18, which serves as a cell and may be made of polystyrene. A suitable ring would be one which has an inner diameter of 6 mm, an outer diameter of 10 mm and a height of 5 mm. The ring may be attached to the prism by putting a drop of toluene between the underside of the ring 18 and the prism 14. The solutions to be examined may be introduced into the cell 18 and sucked up from it without removing the prism from the measuring arrangement. In FIG. 2, a solution 19 is present in the cell. Instead of using a cell in the form of a ring or the like it is of course also possible to conduct measurements by the immediate application to the layer 17 of drops of the solutions to be examined.

EXAMPLE

The test solution as schematically depicted in FIG. 2 was used in an examination of several protein solutions. Three protein solutions were successively introduced into the cell of the measuring arrangement, viz:

| a. anti-HCG 147[b] | 100 mg/l |
|---|---|
| b. BSA | 100 mg/l |
| c. HCG | 100 mg/l |

The solutions were solutions in phosphate buffer, pH 7.5. Beforehand and in between introduction of the various solutions, the cell was rinsed with a clear buffer solution. The results are given in the graph of FIG. 3.

In the graph, the thickness in nm of a built-up protein layer is plotted against the time in minutes. The part of the curve 20 before $t=0$ relates to rinsing with the clean buffer solution. At $t=0$ the anti-HCG 147[b] was introduced into the cell (arrow a in the graph). Within a minute, a layer of about 4 nm was found to have built up. This thickness remains virtually constant over time in spite of rinsing around $t=4$. At $t=6$ the BSA solution was introduced into the cell (indicated by the arrow b in the graph). This turned out to have next to no influence on the thickness of the layer already present. After rinsing around $t=7$, the HCG solution was introduced into the cell shortly after $t=8$. In a very short period of time, the thickness of the layer therefore increased to almost 6 nm.

The example shows that the process according to the invention is highly suited to demonstrating the presence of certain proteins.

I claim:
1. A process comprising radiating a carrier having a thin layer coated thereon with a plane polarized light beam at a single incident angle, detecting the reflectance on the carrier and layer, splitting the light reflected by the carrier and the thin layer into a p-polarized part and an s-polarized part, after which the respective intensities $(I_s)r$ and $(I_p)_r$ of the reflected s-polarized and p-polarized light are measured simultaneously for the two parts, and calculating a quantity M according to the equation:

$$M = \frac{(I_s)_r - (I_p)_r}{(I_s)_r + (I_p)_r} = \frac{R_s - mR_p}{R_s + mR_p},$$

in which
$R_s$ is the ratio of the intensities $(I_s)_r$ and $(I_s)_i$ of the reflected and incident s-polarized light, respectively;
$R_p$ is the ratio of the intensities $(I_p)_r$ and $(I_p)_i$ of the reflected and incident p-polarized light, respectively;
m is the ratio of the intensities $(I_p)_i$ and $(I_s)_i$ of the incident p- and s-polarized light, respectively;
the quantity M being a function of the thickness of the thin layer.

2. A process according to claim 1, wherein use is made, for determining the degree of growth of organic layers on a carrier, of a carrier previously coated with a thin layer of a transparent inorganic material or of an organic polymer of such a thickness that there is an almost linear relation between the quantity M and the thickness of the organic layer built up on the previously applied thin layer.

3. A process according to claim 2, wherein a carrier is used which is coated with a thin layer of transparent inorganic material or of an organic polymer of such a thickness that there is an almost linear relation between the quantity M and the thickness of the organic layer built up on the previously applied thin layer.

4. A process according to claim 1, wherein the carrier comprises a prism, with the light being directed to the prism in such a way that it will enter and leave through the respective lateral faces and be reflected on the base face on which the thin layer is present.

5. A process according to claim 1, wherein said carrier radiating step, said reflectance detecting step, said reflected light splitting step, said reflected s-polarized and p-polarized light measurement steps, and said M calculation step are applied a number of times using, in succession, different protein solutions as the thin layer applied to the carrier to determine protein/carrier and protein/protein interactions.

6. An apparatus for use in determining the thickness of a layer, comprising a substrate for carrying said layer, a beam splitter, a laser source for directing a plane polarized beam toward said substrate, said plane polarized beam being reflected by said substrate and said layer toward said beam splitter, said beam splitter splitting the reflected polarized beam into a p-polarized beam and an s-polarized beam, a first detector for detecting an intensity of said p-polarized beam and a second detector for detecting an intensity of said s-polarized beam and a processing unit for calculating a quantity $$M = \frac{(I_s)_r - (I_p)_r}{(I_s)_r + (I_p)_r} = \frac{R_s - mR_p}{R_s + mR_p}$$

in which
$R_s$ is the ratio of the intensities $(I_s)_r$ and $(I_s)_i$ of the reflected and incident s-polarized light, respectively;
$R_p$ is the ratio of the intensities $(I_p)_r$ and $(I_p)_i$ of the reflected and incident p-polarized light, respectively;
m is the ratio of the intensities $(I_p)_i$ and $(I_s)_i$ of the incident p- and s-polarized light, respectively; and the quantity
M is a function of the thickness of the thin layer.

7. An apparatus according to claim 6, further comprising a cell for containing liquid, said substrate being provided in said liquid.

8. An apparatus as recited in claim 7 wherein said liquid comprises a protein solution.

9. An apparatus as recited in claim 6, wherein said polarized beam hits said substrate at approximately the Brewster angle.

10. An apparatus as recited in claim 6, wherein said laser source is a helium neon laser.

11. An apparatus as recited in claim 6, wherein said substrate comprises a silicon slide coated with a layer of polystyrene.

12. An apparatus as recited in claim 11, wherein said layer of polystyrene is about 50 to 60 nm thick.

13. An apparatus as recited in claim 11, wherein a polarization direction of said polarized beam is 30° to a plane of incidence.

14. An apparatus as recited in claim 6, wherein said substrate comprises an organic polymer layer of a thickness of at least $$0.1 \frac{\lambda}{n}$$

where $\lambda$ is the wavelength of the polarized beam and n is the refractive index of said organic polymer layer.

15. An apparatus as recited in claim 6, wherein said substrate comprises an equilateral prism.

16. An apparatus as recited in claim 15, wherein said equilateral prism is made of heavy flint glass.

17. An apparatus as recited in claim 15, wherein equal planes of said equilateral prism are provided with an antireflection coating and a base face of said equilateral prism is coated with a thin layer of polystyrene.

18. An apparatus as recited in claim 15, wherein a base face of said equilateral prism includes a ring into which solutions to be examined are introduced.

19. An apparatus as recited in claim 15, wherein said laser source is a semiconductor laser.

20. An apparatus as recited in claim 15, wherein the polarization direction of said polarized beam is 8.05° to the plane of incidence.

* * * * *

UNITED STATES PATENT AND TRADEMARK OFFICE
CERTIFICATE OF CORRECTION

PATENT NO. : 4,908,508

DATED : March 13, 1990

INVENTOR(S) : Gerrit C. DUBBELDAM

It is certified that error appears in the above-identified patent and that said Letters Patent is hereby corrected as shown below:

Column 2, line 28, change "$(I_s)r$" to --$(I_s)_r$--.

Column 6, line 44, change "$(I_s)r$" to --$(I_s)_r$--.

Signed and Sealed this

Ninth Day of July, 1991

Attest:

HARRY F. MANBECK, JR.

Attesting Officer

Commissioner of Patents and Trademarks